United States Patent [19]

Wiktor et al.

[11] Patent Number: 4,664,912
[45] Date of Patent: May 12, 1987

[54] PROCESS FOR THE LARGE SCALE PRODUCTION OF RABIES VACCINE

[76] Inventors: Tadeusz J. Wiktor, 9 Downs Circle, Wynnewood, Pa. 19096; Bernard J. Fanget, Le Vignolet, Fleurieux sur l'Arbresle 69 210, France; Pierre Fournier, 59bis Avenue du Point du Jour, 69 005 Lyon, France; Bernard J. Montagnon, Le Bourg Lentilly, 69 210 L'Arbresle, France

[21] Appl. No.: 656,762

[22] Filed: Oct. 1, 1984

[51] Int. Cl.$^4$ .................. A61K 39/205; C12N 7/00; C12N 7/08
[52] U.S. Cl. .................................. 424/89; 435/235; 435/236; 435/237; 435/239
[58] Field of Search .................. 424/88, 89; 435/68, 435/235, 237, 236, 239

[56] References Cited

U.S. PATENT DOCUMENTS 4,347,239 8/1982 Bass et al. ........................ 424/89
4,525,349 6/1985 Montagnon et al. ............... 424/89

OTHER PUBLICATIONS

Chemical Abstracts, vol. 97, Abstract No. 11682c, 1982.

Primary Examiner—Blondel Hazel
Attorney, Agent, or Firm—Cushman, Darby & Cushman

[57] ABSTRACT

In the large-scale production of rabies vaccine a cell stock comprising a VERO cell strain and a liquid nutritive medium containing serum and microcarriers suspended therein is successively passed into biogenerators of increasing volume. The last of the passages is carried out in a biogenerator having a volume of at least 150 liters. The liquid nutritive medium is drawn off at the end of the final passage and replaced with a serum-free liquid nutritive medium. The cell stock is inoculated in the last passage biogenerator with virus which is allowed to develop. The virus is then cultured, withdrawn and filtered. The filtered liquid suspension is then ultrafiltered, with inactivated beta-propiolactone and purified by zonal centrifugation or chromatography.

4 Claims, No Drawings

PROCESS FOR THE LARGE SCALE PRODUCTION OF RABIES VACCINE

The object of the present invention is to provide a process for the large-scale production of a rabies vaccine which is economically satisfactory and easy to use.

Several types of vaccines have been produced since 1885, the date at which the first vaccine against rabies developed by Pasteur was introduced.

There were first of all the vaccines produced on nerve tissue and then inactivated of the Fermi, Semple, Hempt or Fuenzalida type. Then, in order to reduce the secondary effects, a great step was made with the vaccine cultivated on the embryo of the duck (1955). This vaccine remained the reference vaccine for 25 years before the arrival of vaccines produced on tissue culture (1978).

The latter, which are still being used, made a distinct progress in the anti-rabies therapeutics by their high antigenicity and their quasi-absence of secondary effects. The sole criticism which may be made of this type of vaccine is their high cost and difficulty of producing them in a large quantity. All these criteria have for result that the vaccines obtained on tissue cultures (mainly on human diploid cells) are reserved for the curative treatment of rabies.

There is consequently a big place for a highly antigenic vaccine which is of a satisfactory price and can be produced in large numbers.

Very considerable progress has been made in the field of the production of vaccines against viruses such as poliomyelitis with, on one hand, the development of cell lines which are easily reproducible on a large scale, and, on the other hand, microcarriers for cells which permit effecting cell cultures in suspension in nutritive media at a large volume (see for example A. L. VAN WEZEL: New Trends of the Preparation of Cell Substrates for the Production of Virus Vaccines. Progr. Immunobiol. Standard, Vol. 5, pp. 187-192 (Karger, Basel 1972) and Tissue Culture Technology in Virus Vaccine Production, Symposium on "Tissue Culture Technology" at the 75th National Meeting of the American Institute of Chemical Engineers, Detroit, Mich., U.S.A., June 3-6, 1973).

A few years ago, VAN WEZEL mentioned in a publication the use of a line issuing from cells of the kidney of the African green monkey described by YASAMURA Y. in the Establishment of a Cell Strain Derived from Monkey Kidney (C. Aethiops), 14th Meeting of the Jap. Tissue Culture Association October 1962 in TOKYO and available at the American Type Culture Collection under number ATCC-CCL 81 (124th passage). This line is known under the name VERO.

More recently, other processes for producing rabies vaccines have been published. This is the case of VAN WEZEL, et al., "Vaccinations in the Developing Countries, La Guadeloupe 1978: New approach to the production of concentrated and purified inactivated polio and rabies tissue culture vaccines" Develop. Biol. Standard. Vol. 41, pp. 159-168 (S. Karger, Basel 1978). VAN WEZEL thus shows that it is possible to prepare a vaccine against rabies from primary cells of the dog kidney trypsinized and cultivated on microcarriers. However, the rate of harvest of the virus is not very high and the use of primary cells results in high cost without allowing mass production. ATANASIU et al., 1981; Joint ESACT/LABS Meeting on the use of Heteroploid and other cell substrates for the Production of Biologicals; Heidelberg, FR Germany, 1981 "Evaluation and comparative studies of inactivated rabies vaccine obtained in the heterologous diploid and polyploid cells". Develop. Biol. Standard. 50, pp. 173-182 (S. Karger, Basel 1982), compare the features of rabies antigens obtained by the culture in suspension on respectively HAK (Hamster adult kidney), BHK (Baby hampster kidney) and VERO previously cultivated in monolayers. He concludes that, while HAK and VERO form new candidates for the production of inactivated rabies vaccines, the VERO line only provides a small production of virus if it is compared with the other cells.

Owing to these facts and probably to the difficulties of transposing knowledge acquired about one virus to another virus of different type, the prior art has not suggested the mass production of rabies vaccine which is purified and stable and has a high antigenic power from cell lines.

Among all these researches none has resulted up to the present time in a new vaccine which satisfies the criteria mentioned in the introduction.

An object of the present invention is to provide an anti-rabies vaccine satisfying all these criteria.

Another object of the invention is to provide a process for providing a highly purified stable vaccine.

A further object of the invention is to provide such a process for producing a vaccine which has a high antigenic value for a small volume.

The process according to the invention comprises the following steps: multiplying a cell line, preferably a VERO line, from a working seed, by culture on microcarriers in suspension by successive passages in biogenerators of increasing volume, the last passage being effected in a biogenerator whose vat is of at least 150 liters, the ideal volume being 500 or 1000 liters, in a suitable nutritive medium, drawing off the liquid medium at the end of the last passage and replacing it by a new liquid medium containing no serum, inoculating the biogenerator of the last passage with virus, preferably maintaining the temperature in the neighborhood of 35° C. to 37° C., the pH in the neighborhood of 7.4 to 7.8 and the partial pressure of oxygen in the neighborhood of 10 to 50%, drawing off the liquid suspension after culture of the virus, filtering the drawn-off suspension, concentrating at least 100 times by ultra-filtration the filtered suspension, inactivating by the action of Beta-Propiolactone, purifying by zonal centrifugation or chromatography in respect of each of the successive harvests.

The final stage of the process comprises mixing the purified harvests, effecting a dilution as a function of the antigenic titration and adjusting the final formulation so as to prepare unit doses of anti-rabies vaccine.

Preferably, in starting with the VERO working seed, a passage is effected in a 1 liter biogenerator. The cells are obtained by digestion with a very purified and diluted protease solution, then a passage is effected in a 5 liter biogenerator; then a new passage is effected in a 25 liter biogenerator; then a new passage is effected in a 150 liter biogenerator, and a last passage is effected with the use of a biogenerator of very large volume (for example 1000 liters), or a plurality of biogenerators of smaller volume (for example 150 liters), the inoculation by the virus being effected in this last passage.

A very important step from the point of view of production on an industrial scale resides in the passage from one biogenerator to another and a very purified and diluted protease is used in situ in the vat itself, from the 1 liter biogenerator up to that of 1000 liters. Preferably there is employed a very diluted crystallized purified Trypsine solution at betwen 0.005% and 0.05%, and preferably 0.025%. For this purpose, after having drawn off the culture medium, the culture is washed with a suitable buffer so as to eliminate traces of serum coming from the culture medium, the purified and diluted Trypsine solution is added and the product is allowed to incubate (for example for 10 to 15 minutes) while supervising the detachment of the cells from the microcarriers and then the action of the enzyme is blocked by adding a small quantity of serum concentrated medium.

The balls with the cells are recovered in a sterile receptacle with a stirring vibrator, the mixture being passed through continuously with a moderate vibration so as to detach the cells without harming them. The mixture is harvested with veal serum so as to inactivate the Trypsine, then inoculated in a suspension of new balls in the following biogenerator either in a small volume, for example 1/10th of that of the passage of culture proper, thereby facilitating a contact between the cells and the balls, namely in the total volume of the new culture.

The microcarriers employed are preferably spherical balls having a mean diameter of about 50 to 300 $\mu$m in the dry state, having a density very slightly higher than 1, formed either by dextran polymers and carrying on their surface grafted radicals of DEAE (diethyl-aminoethyl), or by acrylic polymers carrying on their surface peptidic groupings, or cross-linked insolubilized proteins. Preferably, the concentration of microcarriers, expressed in weight, namely grams of microcarriers per liter of medium, is between 1 and 10 and preferably between 2 and 5 grams.

The culture temperature is kept at between 35° C. and 38° C. and may be lower so as to permit the survival of the cells in a slowed-down growth phase (for example between 25° and 33° C.).

Preferably, each passage lasts 5 to 8 days, with a stirring, and there is usually observed at the end of the culture a multiplication 8 to 30 times the cell growth.

The stirring is a critical point of the process in large-size biogenerators. Preferably, this stirring is carried out at a rate of 10 to 40 rpm (for example with a stirrer rotating about a vertical axis and having triangular blades one side of which is provided with a fin which makes a rather small angle with the plane of the fin), such as that for example described in French patent No. 80 18608 filed on Aug. 27, 1980.

The culture medium for the passages of cells is preferably a usual medium, such as the Minimum Essential Medium of Eagle enriched with Lactalbumine, Hydrolysate, Glucose, and Veal serum or the like. or a Minimum Essential Medium of Eagle Dulbecco modified, Iscove modified, enriched with Hepes (sulfonic ethane(2-[2-hydroxy-ethyl)-1-piperazinyl]-acid), Veal serum, Metal Salts.

For the viral infection, the culture medium employed both for effecting the cell growth and for the start of the viral proliferation, is the Minimum Essential Medium of Eagle enriched with Glucose containing 1/5 of Veal serum.

The viral inoculation is effected in the course of the last passage with the Pitman-Moore PM 1503-3 M strain with a multiplicity of infection (MOI) between 1 and 0.001.

Two to three days after the infection, a rinsing is effected and the medium is changed with the viral culture medium, Minimum Essential Medium enriched with human albumin serum at 0.05 to 0.3% and preferably 0.1%.

Five to seven days after the infection the viral harvest can be commenced. As the rabies virus is only slighly lytic with respect to the VERO cell, multiple harvests are possible up to 10 but preferably 6.

Each of the harvests will be treated separately and in an identical way until purification.

The sequence of operations common to each harvest comprises a filtration of the raw harvest, a concentration by ultrafiltration and then inactivation by Beta-Propiolactone and purification.

All of the checked, purified and inactivated harvests from the same batch will give a final bulk product.

The vaccine obtained according to the process described hereinbefore contains at least 2.5 International Units per ml determined by the "NIH test" reference method.

By way of example, an individual dose at a volume of 0.5 ml after reconstitution contains, in addition to the 2.5 UI of rabies antigen, 5% of human albumin serum, 5% of maltose, all of which is in the BME medium of Eagle.

The antibiotics employed in the course of manufacture can no longer be measured in the finished product owing to the purification effected.

The invention will now be described by way of a non-limiting example.

1. Cell Multiplication

The VERO line as distributed by the American Type Culture Collection under number ATCC-CCL 81 is used. This cell is at its 124th passage. A cell working seed obtained during the 137th passage is prepared in the conventional manner. The seed is divided up in phials and preserved in liquid nitrogen. Each phial contains about $100 \times 10^6$ cells.

Before preparing a working seed stock, a master seed stock is prepared. With the phial at the 124th passage coming from the ATCC, subcultures are prepared by successive passages up to the 129th passage. After trypsination of the cell strain the cell suspension is homogenized and then divided in phials for storage in liquid nitrogen.

For preparing the working seed one starts with a phial of the the master seed at the 129th passage and one effects a series of subcultures in Roux boxes up to and including the 135th passage by progressively increasing the number of boxes. The 136th and 137th passages are effected in 20 liter and 150 liter biogenerators. At this level the cell population, after trypsination and homogenization, is divided up in phials in the proportion of 100 to $120 \times 10^6$ cells per phial. Several hundreds of phials are sealed and deep frozen in the liquid nitrogen at this stage.

The liquid medium used for the successive passages, including for the establishment of the cell stock, is the Minimum Essential Medium of Eagle in a saline solution of Earle enriched with 0.2% of Lactalbumine hydrolysate, 0.1% of Glucose or Fructose, 5% of Veal serum; it may also be in the Minimum Essential Medium of Eagle in a saline solution of Earle according to the modifications of Dulbecco and Iscove, enriched with 3% of Veal Serum, the osmolality is adjusted to a value between 300 and 350 mOsm/kg and preferably 320 mOsm/kg per addition of sodium chloride and potassium chloride.

This medium may also be completed with metal ions, for example zinc, iron, nickel, copper, vanadium, aluminum, manganese, cadmium, cobalt, chromium, molybdenum, rubidium, tin, titanium, zirconium. Each milliliter of medium contains 75 units of Streptomycine, 14 units of Neomycine and 35 units of Polymyxine B sulfate.

The microcarrier balls employed are DEAE Dextran balls sold under the trademark DYTODEX-1 by the Swedish firm PHARMACIA. In the dry state, the balls have a mean diameter of about 67 micrometers, with a density of 1.03. A gram of dry balls contains approximately $5 \times 10^6$ balls, which corresponds to a total area per gram of about 0.6 m$^2$. The concentration of balls per liter of medium is on the order of 1 to 5 g/l. These microcarrier balls may also be acrylic resin balls, covered with proteins rendered insoluble, sold under the trademark MICARCEL by the French firm I.B.F. These balls have a mean diameter of 180 to 200 micrometers with a density of 1.03.

In order to prepare the balls, they are first of all allowed to inflate in a buffer solution, they are washed and then sterilized, for example in a vat of at least 150 liters while stirring.

In order to effect the multiplication, the contents of a phial at the 137th passage is introduced into a biogenerator containing a liter of medium with the balls according to the aforementioned density. The culture is effected at a temperature of 37° C. for 6 to 7 days, while stirring at 20 revolutions per minute, this stirring being gradually increased.

At the end of the growth, i.e. after the 6th or 7th day, the liquid medium is discharged and the cells are retained, these cells being fixed on the balls. The cells are detached with an 0.025% solution of crystallized Trypsine, buffered with 0.125M sodium citrate. The cells which have thus just undergone their 138th passage are then transferred into a 5 liter biogenerator where the 139th passage is effected in the same way and under the same conditions. A 140th passage is then effected in a biogenerator containing 25 liters of medium and then the 141st passage is effected in a 150 liter biogenerator. The 142nd passage is then effected in a 1000 liter (or 500 liter) vat containing 1000 liters (or 500 liters) of medium. The indicated volumes are the useful volumes.

The stirring is carried out in the vats by means of a stirrer comprising a vertical rotary shaft plunging into the liquid suspension and carrying adjacent to its lower end 2 or more blades each having the general shape of a right-angled triangle, one of the sides of the right angle, preferably the larger, of which is welded along a vertical generatrix of the shaft, the right angle being substantially at the lower end of the shaft. The blades are consequently located in one or more radial vertical planes with the second side of the right angle being substantially horizontal and extending radially at the lower end. Each second side is extended downwardly by a rather short rectangular fin which makes an angle of 10° to 45° with the plane of the blade, the fin having a rectangular shape, one of the larger sides of which conincides with said second side of the right angle. The area of the fin is between ½ and 1/10 of the area of the triangular blade.

The size of the stirrer of course increases with the volume of the vat. On the other hand, the speed of rotation decreases each time one passes to a vat of larger volume, for example from 40 rpm for the vat of 1 liter to 7 rpm for the vat of 1000 liters.

2. Multiplication of the Virus

The viral strain is the same as that employed at the present time for the rabies vaccine produced on human diploid cells, it concerns the strain PM-1503-3 M.

In order to produce the viral infection, the stirring is stopped, the balls covered with cells become deposited at the bottom of the vat so that it is possible to draw off the culture medium. A sufficient quantity of a maintenance medium, MEM, enriched with 1% of Veal serum, is introduced into the vat so as to obtain a homogeneous stirring. At that moment, the viral seed can be introduced so as to start the contact stage.

Two infection ways are possible:

(A) A direct infection of the biogenerator by the viral strain during the exponential stage of the growth of the cells. By way of example, if a maximum cell concentration of $2 \times 10^6$ cells per ml is anticipated, the infection will be effected when the cell concentration will be about $1 \times 10^6$ cells per ml. The quantity of viral seed will be adjusted in such manner as to obtain a MOI of 1 to 0.001.

(B) An infection by cell mixing.

This mode of infection requires the starting up of a culture at the 142nd passage at the same time as the last cell culture stage and with the same cells. This culture, to which is added a volume which is 1/30 th of that of the principal culture, will be infected as soon as it is put into culture by the viral strain in the proportion of a MOI of 0.001 to 0.1. The maintenance of the cell infection is effected by means of the flourescent antibody method. When 100% of the cells are infected, the annex culture is used for infecting the principal culture.

For an industrial production, the infection mode will preferably be that described at (A).

After the virus-healthy cells contact, the volume is completed to the total volume of the culture.

Two to three days after the infection, when the cell growth stage has finished, there are effected the rinsings (3) of the balls plus the cells with the virus medium. The medium is replaced by the MEM medium containing 0.1% of human albumin. The culture parameters are consequently adjusted: temperature 35° C., pH 7.50, PO$_2$ 25%.

About 7 days after the day of infection, a first harvest, termed "R$_1$", is effected. The stirring of the biogenerator is stopped, the microcarrier balls become deposited, the medium is drawn off by aspiration, it is the harvest proper.

There is added the viral propagation, MEM with 0.1% of human albumin, the stirring is recommenced and the product is held at 35° C. for 3 or 4 days until the following harvest, and so on. A succession of harvests: R$_1$-R$_2$ ... R$_6$ ... is consequently obtained.

3. Concentration-Inactivation

Each of the harvests is immediately filtered at 0.45 micron before the concentration step. The harvest is subjected to an ultrafiltration on a Millipore membrane of polysulfone whose molecular separating power is at a molecular weight of 10,000 or 100,000. It is also possible to contemplate the use of membranes having a cut-off threshold in the neighborhood of one million. The filtering liquid, i.e. the ultrafiltrate, is discarded and the retained part is kept. By this process, the volume of each harvest is thus reduced by a factor 25. The inactivation is carried out on the concentrated viral product.

The inactivation step (less than 72 hours after the filtration) consists in putting the Beta-Propiolactone (BPL) in contact with the viral suspension at a concentration of 1/4000, namely 0.025%.

By way of example, a schematic description of the method employed will now be given:

The BPL solution prepared extemporaneously on ice water is added to the viral suspension while constantly stirring. Eight hours after the end of the addition of the BPL, a transfer is effected in a new flask. After 234 hours at +4° C., the viral suspension is heated to 37° C. and maintained at this temperature for 2 hours.

4. Purification

Each inactivated harvest is then concentrated a second time according to the procedure described in paragraph 3 so as to reduce the volume to be purified by a factor 4. The concentration factor thus obtained is 100 relative to the starting product.

At this stage, each of the harvests may be stored at the temperature of $< +45°$ C. while awaiting purification.

The purification is carried out by a zonal centrifugation in a sucrose density gradient. At the end of the operation, the purified virus fractions are gathered and mixed: the volume thus obtained is diluted with a Tris-/EDTA/NaCl (TEN) buffer so as to obtain a concentration factor of 150 relative to the starting product.

The purification is carried out with a zonal rotor usually of the type B 15. The various sucrose solutions are prepared with a TEN buffer, pH 7.8.

The centrifugation conditions are:

| | |
|---|---|
| concentrated virus brought to | 1200 ml |
| 34% sucrose solution (P/P) | 370 ml |
| 60% sucrose solution (P/P) | 100 ml |
| centrifugation for 4 hours at 25,000 rpm at +4° C. | |

This purification method has a limiting factor, the number of cycles to be effected. This is why chromatographic methods are preferred for mass production.

The chromatographic purification will associate a gelfiltration step with an ion exchange column.

The molecular screening column (gelfitration) containing an agarose gel, for example SEPHAROSE CL 4 B or TRISACRYL G 2000, or a modified Spherosil, permits the elimination of the proteins and other impurities, the larger viral particles being excluded first of all.

In order to refine the purification, the addition of an ion exchange column DEAE-Dextran-Silice (SPHERODEX) enables the remaining impurities to be fixed, the virus travelling freely through the column.

5. Preparation of the Final Product

A plurality of satisfactory purified individual harvests are mixed. According to the antigenic titration of the pool of the harvests, the dilution to be effected is determined. The final volume is adjusted in order to have a concentration of maltose and human albumin of 5% in an Eagle BME medium at ½, in distilled water and to have a dose at a volume of 0.5 ml.

The product is divided up and freeze dried in a sterile premises.

Each bottle of lyophilized vaccine is taken up with 0.5 ml of solvent (4 g/l NaC solution).

6. Checks

The vaccine was checked from the point of view of its antigenic activity, of the NIH potency at +4° C. and 37° C., its bacterial and fungus sterility and its toxicity.

Further, tumourigenicity of the VERO cells tests were carried out on newly-born rats. The tests were negative.

The quantities of cell DNA detected after purification are extremely small.

7. Clinical Tests

Table I summarizes the side effects actively observed during the follow-up of 328 injections given in France to 174 healthy adult volunteers. Local reactions observed included erythema at the injection site (4%), and induration (3.3%), mainly seen during the two days following the injection. Slight local pain was reported in 6.7% of cases, with a maximum effect 24 hours after the injection. General reactions observed in the same subjects included:
 fever of more than 38° C. in 0.9% of cases
 slight asthenia for between 2 and 48 hours after one of the injections.

Table II shows the booster effect observed in 86 subjects previously immunized with traditional HDCS vaccine, of whom approximately 84% presented residual antibodies at the time of injections with a single 0.5 ml dose of PVRV. A month after the booster injection, all subjects presented high antibody titres: the range being from 1.6 to 189 with a geometric titre (GMT) of 18 IU per ml.

Table III summarizes one of the primo-immunization trials in 64 healthy volunteers who had never been vaccinated against rabies. The pre-exposure vaccination schedule was that recommended by the American authorities, and consisted of 3 subcutaneous injections of 0.5 ml each on days 0, 7 and 21. No subject presented antibodies before the first injection.

TABLE I

PVRV SAFETY - LOCAL AND GENERAL SIDE EFFECTS OBSERVED AFTER 328 INJECTIONS

| | NUMBER | PERCENTAGE |
|---|---|---|
| ERYTHEMA | 13 | 4% |
| INDURATION | 11 | 3.3% |
| SPONTANEOUS PAIN | 22 | 6.7% |
| FEVER | 3 | 0.9% |
| ASTHENIA | 8 | 2.4% |

TABLE II

PVRV - BOOSTER EFFECT

| | NUMBER OF SUBJECTS | GMT IU/ML | PERCENTAGE TITER > 0.5 |
|---|---|---|---|
| BEFORE BOOSTER | 86 | 2.15 | 83.7% |
| 1 MONTH AFTER BOOSTER | 86 | 18.0 | 100% |

TABLE III

PVRV RESULTS AFTER PRIMO-IMMUNIZATION USING 3 INJECTIONS (D 0, 7, 21)

| | NUMBER OF SUBJECTS | GMT IU/ML | PERCENTAGE TITER > 0.5 |
|---|---|---|---|
| BEFORE IMMUNIZATION | 64 | 0 | 0% |
| 1 WEEK AFTER 2 INJECTIONS | 64 | 28.2 | 100% |
| 3 WEEKS AFTER 3 INJECTIONS | 64 | 32.4 | 100% |

What is claimed is:

1. A process for the large-scale production of rabies vaccine comprising
   (a) successively passing into biogenerators of increasing volume a cell stock comprising a VERO cell strain and a liquid nutritive medium containing serum, said liquid nutritive medium having suspended therein microcarriers present in an amount ranging from 1 to 10 grams per liter of said liquid nutritive medium, each such passage being carried out with stirring at a rate not greater than 40 rpm and for a period of time ranging from 5 to 8 days, the last of said passages being carried out in a biogenerator having a volume of at least 150 liters,
   (b) drawing off said liquid nutritive medium at the end of the final passage and replacing said liquid nutritive medium with a serum-free liquid nutritive medium,
   (c) inoculating said cell stock in the last passage biogenerator with virus and allowing the virus to develop at a temperature between 35°–37° C. at a pH of about 7.4 to 7.8 and at a partial oxygen pressure of about 10–50 percent while stirring at a rate not greater than 40 rpm,
   (d) culturing the said virus for a period of at least 5 days,
   (e) withdrawing the liquid suspension of cultured virus,
   (f) filtering the withdrawn liquid suspension,
   (g) ultrafiltering the filtered liquid suspension so as to concentrate the same at least 100 times,
   (h) inactivating the concentrated suspension with beta-propiolactone and
   (i) purifying the inactivated suspension by zonal centrifugation or chromatography.

2. The process of claim 1 wherein the liquid nutritive medium withdrawn in step (b) is contacted with a dilute solution of purified protease so as to separate the cells from the microcarriers.

3. The process of claim 1 wherein said cell stock is inoculated in step (c) with a Pitman-Moore PM 1.503-3 M rabies virus strain.

4. The process of claim 1 wherein the molecular separating power of the ultrafiltration in step (g) is at a molecular point of 10,000 to one million.

* * * * *